United States Patent [19]

Somlo et al.

[11] Patent Number: 4,507,240

[45] Date of Patent: Mar. 26, 1985

[54] PROCESS FOR PURIFYING CRUDE MONOCHLORO- AND MONOBROMOANTHRAQUINONE

[75] Inventors: Tibor Somlo; Johann Regli, both of Birsfelden, Switzerland

[73] Assignee: Ciba-Geigy AG, Basel, Switzerland

[21] Appl. No.: 554,651

[22] Filed: Nov. 23, 1983

[30] Foreign Application Priority Data

Nov. 29, 1982 [CH] Switzerland ............... 6922/82

[51] Int. Cl.$^3$ ........................................ C07C 50/24
[52] U.S. Cl. ................................. 260/384; 260/694
[58] Field of Search .................................... 260/384

[56] References Cited

U.S. PATENT DOCUMENTS 1,969,044  8/1934  Shaw et al. ............... 260/384
2,587,093  2/1952  Belshaw et al. ............ 260/383

FOREIGN PATENT DOCUMENTS 2522177  11/1976  Fed. Rep. of Germany ...... 260/384
178390    2/1966   U.S.S.R. ...................... 260/384

Primary Examiner—Glennon H. Hollrah
Assistant Examiner—Raymond Covington
Attorney, Agent, or Firm—Edward M. Roberts; Kevin T. Mansfield

[57] ABSTRACT

A process for purifying crude monochloro- or monobromoanthraquinone is described. In this process, monochloro- or monobromoanthraquinone which contains by-products as impurities is mixed with a hot non-polar aliphatic solvent in such a ratio that more than half of the crude product goes into solution and the remainder which contains the impurities forms a second lower phase, said eutectic melt is separated, and the saturated solution is allowed to cool, and the monochloro- or monobromoanthraquinone, which precipitates in pure form, is isolated.

7 Claims, No Drawings

PROCESS FOR PURIFYING CRUDE MONOCHLORO- AND MONOBROMOANTHRAQUINONE

The present invention relates to a process for purifying crude monochloro- and monobromoanthraquinone.

Haloanthraquinones, in particular 1-chloroanthraquinone, are important starting materials for dye synthesis. The purity of these starting materials is of crucial importance for the reproducibility of the shade and for the fastness properties of the dyes prepared therefrom.

It is known that crude chloro- and bromoanthraquinones always contain a number of unwanted by-products which are difficult to separate. Such mixtures of crude reaction products can be purified e.g. by fractional vacuum distillation (DE-OS No. 24 58 022 and DE-OS No. 25 31 929). However, this process has considerable disadvantages. For example, the distillation must be carried out under vacuum and at relatively high temperatures (still temperature of 230° to 270° C. and a sump temperature of about 300° C.) at which temperature the haloanthraquinone to be purified partly decomposes. Further, the pronounced tendency of e.g. 1-chloroanthraquinone to crystallise and sublime makes it necessary to heat all the parts of the apparatus which come in contact with the product, so that complicated steps in respect to the apparatus employed are required. In addition, the haloanthraquinones must be subjected to a pretreatment before the distillation, e.g. washed free of acid, and a further operation is necessary after the distillation in order to convert the product, which is obtained in the form of a melt, into a form which is easy to handle, e.g. a granulate.

Accordingly, it is the object of the present invention to provide a process for purifying crude haloanthraquinones, which does not have the disadvantages referred to above.

It has been found that monochloro- and monobromoanthraquinones are obtained in high technical purity (95 to 99%), in simple manner, by mixing crude monochloro- or monobromoanthraquinone (80 to 90%) with a non-polar aliphatic solvent in such a ratio that, at elevated temperature, more than half of the crude product goes into solution and the remainder which contains the impurities forms a eutectic melt.

The eutectic melt can be readily separated from this two-phase system as lower phase, while the monochloro- or monobromoanthraquinone is isolated in pure crystalline form for easy handling by cooling the saturated solution which forms the upper phase.

Crude monochloro- and monobromoanthraquinone of about 80 to 90% purity can be substantially freed from by-products, such as halogenated bisanthraquinonyls, by the process of this invention, as these by-products, together with specific amounts of monohaloanthraquinone, surprisingly form a readily separable eutectic melt. It is obvious that the desired degree of purity will depend on the requirements which are made of the haloanthraquinones in the course of their further processing to dyes. Depending on the quality requirement, more or less halonanthraquinone must be separated with the eutectic melt.

It is preferred to use the process of this invention for purifying 1-bromoanthraquinone and, most preferably, 1-chloroanthraquinone. However, it can also be used with equally good effect for purifying anthraquinones which are substituted in the 2-position by chlorine or bromine.

Examples of suitable non-polar aliphatic solvents are hydrocarbons or halogenated hydrocarbons with a boiling point above 125° C. Particularly suitable solvents are mixtures of unbranched and/or branched aliphatic hydrocarbons which have a boiling range from 130° to 220° C. and do not contain aromatics and naphthenes. The most preferred mixtures are the mixtures of isoparaffins which have boiling ranges from 155° to 175° C., 170° to 190° C. and 190° to 210° C., and which are available e.g. from ESSO under the trademark Isopar G, H and L.

The procedure for carrying out the purifying process of this invention is conveniently such that the crude monochloro- or monobromoanthraquinone is charged in solid form, or preferably as melt, to the non-polar solvent. The crude product is then dissolved at elevated temperature. Initially the solvent has a temperature above 130° C. but below the temperature of the melt of the pure monochloro- or monobromoanthraquinone, advantageously in the range from 140° to 180° C., or it is heated to a temperature in this range after the addition of the compound to be purified. It is important that crude product and solvent are mixed in such a ratio that not all of the monochloro- or monobromoanthraquinone dissolves at elevated temperature, but that a certain amount, together with the impurities, forms a second phase as eutectic melt.

For example, 90% pure product is charged to a sufficient amount to solvent that about 80% dissolves at elevated temperature and 10% of the undissolved chloro- or bromoanthraquinone, together with the insoluble by-products, forms a eutectic melt.

The temperature of the solvent must therefore be sufficiently high that the undissolved remainder is present in the molten state and separates as a second phase from the saturated solution of the chloro- or bromoanthraquinone. After separation of this phase, the saturated solution is cooled, with stirring, to a temperature of advantageously 20° to 60° C., whereupon the pure chloro- or bromoanthraquinone precipitates.

The temperature and mixture ratios are conveniently so chosen that the eutectic melt contains about two-thirds haloanthraquinone and one third impurities. This ratio can, of course, vary within a certain range, with the lower and upper limit being respectively from 30 to 90% by weight, preferably from 50 to 75% by weight, of haloanthraquinone. The eutectic mixture obtained after several purification operations can be worked up by crystallisation or distillation.

Regardless of its provenance, crude monochloro- or monobromoanthraquinone can be freed almost completely from by-products by the process of this invention. For example, it is possible to purify 1-chloroanthraquinone obtained according to A. Fischer, starting from anthraquinonesulfonic acid by replacement of the sulfonic acid group (q.v. Ullmann, 4th edition, Vol. 7, page 589), or also by reaction of nitroanthraquinone with elementary chlorine (German Reichspatent Nos. 252.578 and 254.450).

As about twice the amount of chloro- or bromoanthraquinone—depending on the degree of impurity—is also separated together with the by-products, preference will naturally be given a process for the preparation of haloanthraquinones, which already yields a fairly pure product.

Readily purifiable crude monochloroanthraquinone with a low content of by-products is prepared by a preferred process by reacting nitroanthraquinone in the termperature range from 180° to 300° C., preferably from 200° to 270° C., with elementary chlorine, in the presence of a solvent which is inert under the reaction conditions and has a boiling point above 180° C. The solvent is added in an amount of 1 to 20% by weight, preferably of 5 to 10% by weight, based on nitroanthraquinone.

The reaction can be carried out e.g. in an agitator vessel equipped with a stirrer for blowing in gas. Suitable solvents are in particular nitrobenzene, sulfolane or hexachlorobutadiene. The solvent evaporates during the reaction, leaving as residue the chloroanthraquinone melt, which can be charged directly to the non-polar solvent for purification without first being isolated and pretreated.

The invention is illustrated by the following Examples.

EXAMPLE 1

A 2½ liter sulfating flask, with bottom outlet, is charged with 1500 g of a mixture of isoparaffins having boiling ranges from 155° to 173° C. (Isopar G/ESSO). To the solvent are then added 380 g of crude 88% 1-chloroanthraquinone and the mixture is heated and stirred for 1 hour at 140° to 145° C. Then the stirrer is stopped, a blackish brown oil which has separated as lower phase is run off, and the residual pale yellow solution is cooled, whereupon pale yellow crystals of pure 1-chloroanthraquinone precipitate. The crystals are filtered with suction at 50° C. and dried in vacuo at 110° C., yielding 300 to 310 g of 1-chloroanthrquinone of 96±1% purity in a form ready for direct use.

EXAMPLE 2

A 1½ liter reaction vessel is charged with 200 parts by weight of nitrobenzene and then 1771 parts by weight of 1-nitroanthraquinone are added at 200° to 210° C. Then about 520 parts by weight of chlorine gas are introduced at 215° to 220° C. over 3 to 4 hours by means of a stirrer for blowing in gas, and the nitrobenzene is distilled off in a separator. When the reaction is complete, the melt is freed from traces of gas and nitrobenzene by briefly blowing off with nitrogen, and cooled to 170° C. The melt is then charged to 6800 parts by weight of a mixture of isoparaffins with boiling ranges from 190° to 211° C. (Isopar L/ESSO), which mixture has been heated beforehand to a temperature from 135° to 140° C. The mixture is stirred for 1 hour at 140° to 145° C., then the stirrer is stopped and the brownish black oil layer is run off through the bottom outlet. After stirring for ½ hour at 135° C., the separation is repeated. The pale yellow solution is then cooled to 50° C. and the precipitated crystals are filtered with suction and dried to constant weight in vacuo at 120° C. Yield: 1360 g of 1-chloroanthraquinone of 96±1% purity.

EXAMPLE 3

A 2½ liter sulfating flask, with bottom outlet, is charged with 1500 parts by weight of a mixture of isoparaffins with a boiling range from 182° to 212° C. (Shellsol T, available from Shell Chemie). Then 400 parts by weight of crude 92% bromoanthraquinone are added, and the mixture is heated and stirred for 1 hour at 175° C. The stirrer is then stopped and a blackish brown oil, which has separated as lower phase, is run off and the residual pale yellow solution is cooled, whereupon bright yellow crystals of 1-bromoanthraquinone precipitate. These crystals are filtered with suction at 50° C. and dried in vacuo at 110° C., yielding 330 g of 1-bromoanthraquinone of 98 to 99% purity.

What is claimed is:

1. A process for purifying crude monochloro- or monobromoanthraquinone, which comprises mixing monochloro- or monobromoanthraquinone which contains by-products as impurities with a non-polar aliphatic solvent in such a ratio that at elevated temperature more than half of the crude product goes into solutions and the remainder which contains the impurities forms a eutectic melt as second lower phase, separating said melt, allowing the saturated solution to cool, and isolating the pure precipitated monochloro- or monobromoanthraquinone.

2. A of process according to claim 1, for purifying crude 1-bromoanthraquinone, in particular 1-chloroanthraquinone.

3. A of process according to claim 1, wherein hydrocarbon or a halogenated hydrocarbon with a boiling point above 125° C. is used as non-polar aliphatic solvent.

4. A of process according to claim 1, which comprises the use of a mixture of unbranched and/or branched aliphatic hydrocarbons having a boiling range from 130° to 220° C.

5. A of process according to claim 1, wherein the solvent, upon separation of the eutectic melt, has a temperature which is above 130° C. and below the melt temperature of the pure monochloro- or monobromoanthraquinone.

6. A of process according to claim 1, wherein the eutectic melt comprises up to 30 to 90% by weight, preferably from 50 to 75% by weight, of monochloro- or monobromoanthraquinone.

7. A of process according to claim 1, wherein the solution of the monochloro- or monobromoanthraquinone is cooled to a temperature in the range from 20° to 60° C. after separation of the eutectic melt.

* * * * *